United States Patent [19]

Lervick

[11] Patent Number: 5,053,207

[45] Date of Patent: Oct. 1, 1991

[54] STERILIZER DEVICE FOR TONOMETER TIPS

[76] Inventor: Dale G. Lervick, 7872 S. Hill Dr., Littleton, Colo. 80120

[21] Appl. No.: 431,988

[22] Filed: Nov. 6, 1989

[51] Int. Cl.$^5$ .......................... A61L 2/18; A61J 1/18; B65D 85/38
[52] U.S. Cl. ................................... 422/300; 422/292; 422/301; 422/302; 422/28; 206/210; 206/369
[58] Field of Search ............... 422/292, 297, 300, 301, 422/302, 309, 28, 63; 436/49; 206/210, 369; 73/80; 118/428, 429, 501

[56] References Cited

U.S. PATENT DOCUMENTS

| | | | |
|---|---|---|---|
| 2,219,417 | 10/1940 | Furr | 21/86 |
| 3,282,090 | 11/1966 | Posner et al. | 73/80 |
| 3,511,085 | 5/1970 | Posner et al. | 73/80 |
| 3,913,390 | 10/1975 | Piazza | 73/80 |
| 4,327,060 | 4/1982 | Nisii | 422/300 |
| 4,382,788 | 5/1983 | Pelerin | 422/300 |
| 4,735,209 | 4/1988 | Foody | 128/652 |
| 4,772,418 | 9/1988 | Leoncavallo | 422/297 |
| 4,824,641 | 4/1989 | Williams | 422/73 |
| 4,868,397 | 9/1989 | Tittel | 422/300 |

FOREIGN PATENT DOCUMENTS 2340132 2/1975 Fed. Rep. of Germany ...... 422/292

OTHER PUBLICATIONS

Van Buskirk, E. M. "Disinfectant Receptacle for Applanation Tonometers", Ophthalm., 1987, 104(3), pp. 307-308.
Nagington, J. et al., "Tonometer Disinfection and Viruses" British Journal of Ophthalmology, 1983, 67, pp. 674-676.
C. L. Chronister et al., "A Simple Guard Against the AIDS Virus", *Review of Optometry*, p. 75, May, 1989.

*Primary Examiner*—David L. Lacey
*Assistant Examiner*—Kimberly A. Trautman
*Attorney, Agent, or Firm*—John E. Reilly

[57] ABSTRACT

A sterilizing device which is specifically adaptable for use with tonometer tips of the removable type comprises a container for a disinfectant solution and has with an upper edge in surrounding relation to an opening into the interior thereof. A lid is disposed on the upper edge of the container with a plurality of spaced tip-supporting openings which releasably support one of the tonometer tips for downward extension from the lid into the solution in the container.

5 Claims, 1 Drawing Sheet

STERILIZER DEVICE FOR TONOMETER TIPS

Specification

This invention relates to sterilizing systems, and more particularly relates to a novel and improved sterilizer device for tonometer tips useful in the field of ophthalmology.

BACKGROUND AND FIELD OF THE INVENTION

Tonometer tips are customarily employed as diagnostic tools by the ophthalmologist and optometrist for measuring ocular pressure to determine the possible existence of glaucoma. In the applanation tonometer an optically transparent tip is releasably mounted in a support housing and disposed on the optical axis of a lens in the housing. The transparent end surface of the tip is placed against the cornea and the ocular pressure is determined by measuring a known force applied over a known area of the corneal contact surface of the tip.

It has long been recognized that at least the corneal contact surface of the tip of the tonometer must be sterilized prior to each measurement or use in order to avoid transmission of disease through tears or lacrimal fluid. The problem of disease transmission has been aggravated in recent years by the recognition of the existence of new diseases and uncertainty as to whether such diseases may be transmitted through tears. For example, much has been written in recent years regarding acquired immune deficiency syndrome (AIDS) caused by infection with the human immunodeficiency virus (HIV). There remains considerable public confusion related to basic facts about the AIDS virus and how it is transmitted. Although HIV has been isolated in the tears of some people with AIDS, tears are not recognized as a mode of transmission. There are no cases of AIDS seroconversion to HIV positive antibody status attributed to tears. Nevertheless, the American Academy of Optometry and the American Academy of Ophthalmology have joined with the Centers for Disease Control in establishing universal infection control protocols. With respect to instruments, the following has been recommended:

"Instruments should be rinsed under running water to remove any organic matter, then disinfected, irrigated with saline and dried. Instruments may be disinfected by heat such as by autoclave for 10 to 30 minutes or by a 10 minute exposure to any of the following fresh (prepared daily) solutions.

1. 0.5% solution (1 to 10 dilution) of common household bleach (sodium hypocholrite)
2. 3% hydrogen peroxide
3. 70% ehthanol
4. 70% isopropyl alcohol.

In recognition of the foregoing, it is to be noted that a soaking period is required for each tip so as to make impractical a temporary or rapid sterilization procedure. For example, one method of sterilization that has been proposed is that disclosed in U.S. Pat. No. 4,735,209 to Foody in which the tonometer has a pivotal housing so that the corneal contact surface can be pivoted into a sterilizing medium without removal from the housing. In U.S. Pat. No. 2,219,417 to Furr, a sterilizer is provided for medical devices which employs a combination of flasks and an electric heating element to boil a sterilizing solution in the flasks and cause the vapors produced to pass through the interior of hypodermic syringes. In U.S. Pat. No. 3,282,090 and 3,511,085 to Posner, et al, means are disclosed for sterilizing tonometers; the '085 patent to Posner, et al., discloses a disposable tonometer tip to facilitate sterilization but does not disclose or suggest a specific means of sterilization. Accordingly, while it is well known to construct applanation tonometers with disposable tips, there is a need for an effective means of sterilization which will facilitate soaking of the tip for any requisite or desired time interval followed by drying and cleaning as a preliminary to each use.

SUMMARY OF THE INVENTION

It is therefore an object of the present to provide for a novel and improved sterilization system specifically adaptable for use in sterilizing tonometer tips.

Another object of the present invention is to provide for a sterilization device for soaking and drying tonometer tips and the like which is compact, inexpensive and at the same time highly dependable and easy to use both by skilled and unskilled personnel.

A further object of the present invention is to provide for a novel and improved sterilization device for tonometer tips which is portable and extremely compact and complies with universal infection control protocols.

In accordance with the present invention there has been devised a sterilizing device which is specifically adaptable for use with tonometer tips and particularly those of the removable type. The device comprises a container for a disinfectant solution, the container provided with an upper edge in surrounding relation to an opening into the interior of the container, and a lid is disposed on the upper edge of the container having a plurality of spaced tip-supporting means, each of the tip-supporting means releasably supporting one of the tonometer tips for downward extension from the lid into the solution in the container. In the preferred form, the tip-supporting means take the form of openings which are sized to releasably support the upper ends of the tips for downward extension into the solution. In addition, the lid is oversized with respect to the upper edge of the container and with at least one opening disposed outwardly of the upper edge of the container so that a tip may be supported in that opening for drying after it is soaked for a predetermined time in the solution.

The above and other objects, advantages and features of the present invention will become more readily appreciated and understood from a consideration of the following detailed description of a preferred embodiment when taken together with the accompanying drawings, in which:

DETAILED DESCRIPTION OF THE PREFERRED EMBODIMENT

Figure 1:
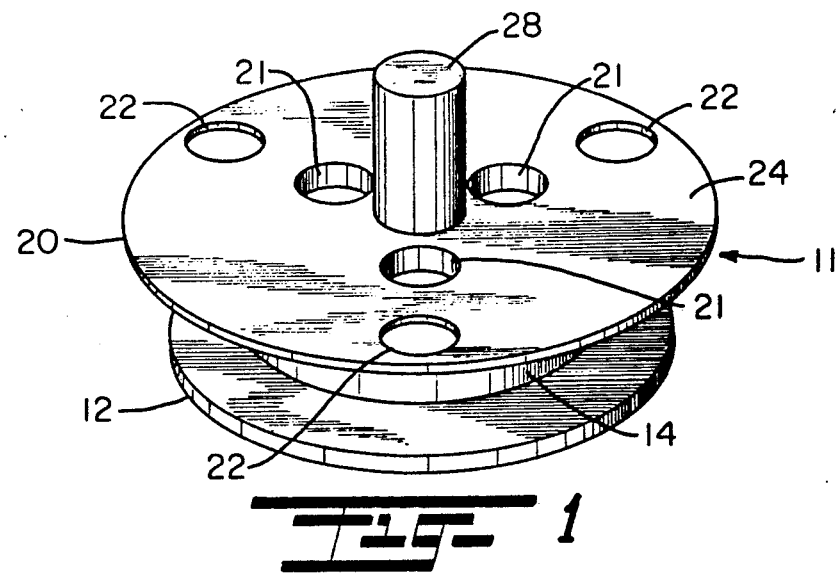
FIG. 1 is a perspective view of a preferred form of sterilization device in accordance with the present invention.
Figure 2:
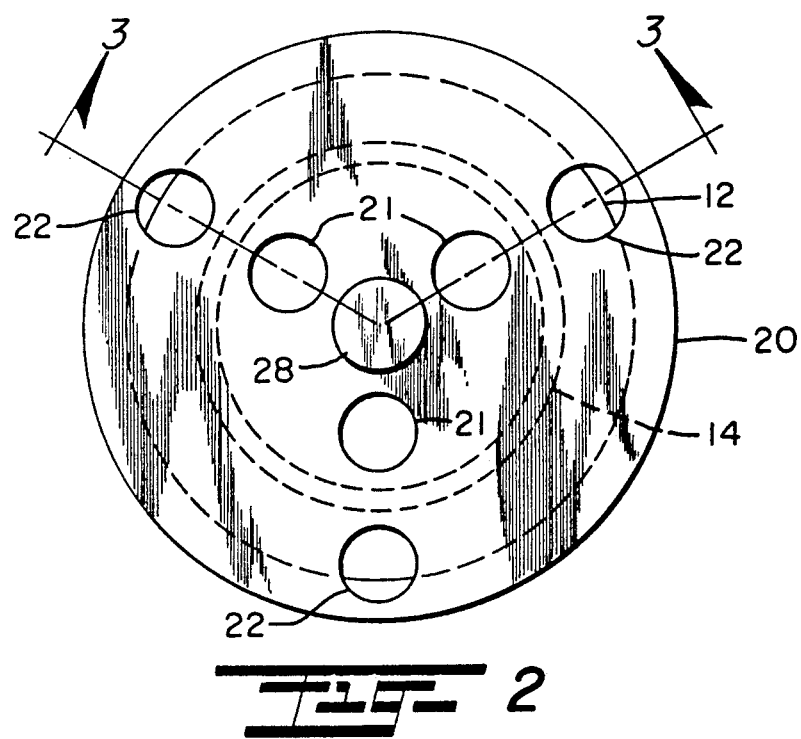
FIG. 2 a top plan view of the sterilization device shown in FIG. 1.
Figure 3:
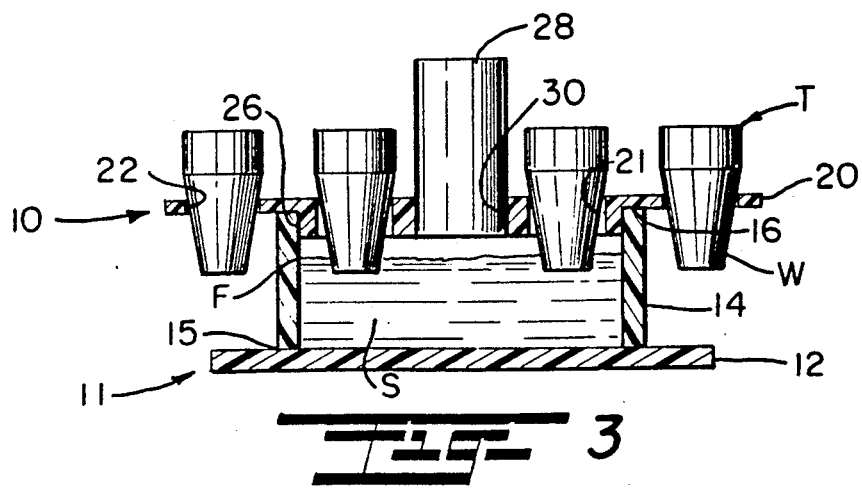
FIG. 3 is a sectional view taken about lines 3—3 of FIG. 2.

Referring in detail to the drawings, there is illustrated in FIGS. 1 to 3 a preferred form of sterilizer device 10 which is specifically intended for use in soaking and drying tonometer tips as represented at T. As a setting for the present invention, the tonometer tip may be a removable tip of an applanation tonometer of the type manufactured and sold by Haag-Streit Service, Inc. of Waldwick, New Jersey, and which is broadly characterized by having a generally cylindrical housing with a downwardly convergent, frustoconical wall W and which terminates in a lower end having a corneal contact surface at its lower end, not shown. Generally, it is important in sterilization of instruments of this type to provide for a means of suspending the tips to a predetermined level into a disinfectant solution but at the sam time not to seal the solution or tip within the solution receptacle; also, it is desirable to provide a method and means for sterilizing several tips at a time and simultaneously drying one or more tips after they have soaked for a predetermined time interval as a preliminary to reuse.

The preferred form of sterilization device 10 is preferably comprised of a container or receptacle 11 having an opaque base or bottom plate 12, and an upstanding generally cylindrical, transparent wall 14 is integrally formed or united to the base 12 along its lower edge 15. The wall 14 also includes an upper circular edge 16 to define an opening or entrance into the container and, for example, to permit filling of the container with a disinfectant solution as designated at S to a predetermined fluid level as indicated at F. It will be seen that the container as described is relatively broad and shallow so as to provide a stable base for supporting a plurality of tonometer tips during the sterilization procedure.

A lid 20 is removably disposed on the upper edge 16 of the container wall 14 and is provided with a plurality of tip-supporting means in the form of spaced openings 21 and 22. The lid 20 is preferably constructed of a flat plate 24 which is oversized with respect to the wall 14 so that outer openings 22 are positioned at spaced circumferential intervals around the lid and radial outwardly of the wall 14. The inner spaced openings 21 are similarly arranged in a circumferential fashion but disposed inwardly of the wall 14 of the container. The lid includes a downwardly projecting circumferential flange 26 which is dimensioned to fit inside of the inner edge of the wall portion 14 so as to center the lid 20 with respect to the wall 14 and minimize accidental displacement or shifting of the lid once in place for the sterilization procedure. In addition, a handle 28 is mounted in fixed relation to a central opening 30 in the lid 20 and extends upwardly from the lid in order to facilitate handling of the lid 20 in placement or removal with respect to the container wall 14.

For the purpose of illustration and not limitation, the container 11 may be composed of glass or any number of plastic materials and most desirably is made up of a clear plastic wall 14, opaque bottom 12 and an opaque top or lid 20. The tip-supporting openings 21 and 22 are correspondingly of circular configuration and sized in a manner such that each tip can be suspended in an opening with the surrounding edge of the opening engaging the conical wall W of the tip and the lower end of that wall W resting in the solution S just sufficient to cover the corneal contact surface at the lower end of the tip. The broad, shallow configuration of the container as shown and described is important from the standpoint of avoiding accidental tipping or breakage of the container or spilling of its contents.

In a typical sterilization procedure, the open container is filled with a 3% hydrogen peroxide solution up to the fluid level F, or a level sufficiently high to cover 5 mm. of the tonometer tip. The lid is placed on top of the container 11 and a tonometer tip T is inserted into one or more of the inner openings 21 to soak for a predetermined time interval usually on the order of 10 to 15 minutes. After soaking, the tip(s) is removed and placed in one of the outer openings 22 in order to air dry the corneal contact surface. The tip is wiped after soaking and drying as a preliminary for use.

It will be appreciated from the foregoing that one or more spaced, tip-supporting openings 21 and 22 may be provided in the lid 20. Moreover, while the lid 20 has been illustrated as being removably positioned by means of a flange in centered relation to container wall 14 it may also be provided with mated threading along the confronting surfaces of the wall 14 and flange 26 to threadedly interconnect the lid to the container.

It is therefore to be understood that the above and other modifications and changes may be made in the precise construction and arrangement of elements and parts comprising the preferred form of present invention without departing from the spirit and scope of the invention as defined by the appended claims.

I claim:

1. A sterilizer device for disinfecting tonometer tips comprising in combination a generally cup-shaped receptacle including a disinfectant solution filled to a predetermined level in said receptacle, and a lid disposed on an upper open edge of said receptacle, said lid having a plurality of circumferentially spaced, inner tip-supporting means therein disposed radially inwardly of said upper open edge of said receptacle for downward extension of a plurality of said tips into said solution, a peripheral portion of said lid extending radially beyond said upper open edge of said receptacle and provided with at least one outer tip-supporting means in said peripheral portion for drying said tips after sterilization, and means for positioning said lid in centered relation to said receptacle.

2. A sterilizer device according to claim 1, wherein said inner and outer tip-supporting means one each defined by an opening in said lid.

3. A sterilizer device according to claim 1, said receptacle being of broad, shallow configuration having an upstanding cylindrical wall and a flat base member extending peripherally beyond said cylindrical wall.

4. A sterilizer device according to claim 3, said lid is an opaque plate oversized with respect to said cylindrical wall, and said inner tip-supporting means are defined by circumferentially spaced openings in said lid located within said cylindrical wall, and said outer tip-supporting means are defined by circumferentially spaced openings located peripherally beyond said cylindrical wall.

5. A sterilizer device according to claim 4, said lid has a handle extending upwardly from said lid, and said positioning means is defined by a circumferentially extending flange on an undersurface of said lid positioned within said upper open edge of said cylindrical wall.

* * * * *